United States Patent [19]

Clingman et al.

[11] 4,446,748

[45] May 8, 1984

[54] PROPORTIONAL FLOW SAMPLER

[75] Inventors: William H. Clingman, Dallas; Kenneth R. Hall, College Station, both of Tex.

[73] Assignee: Precision Machine Products, Inc., Dallas, Tex.

[21] Appl. No.: 325,312

[22] Filed: Nov. 27, 1981

[51] Int. Cl.$^3$ .............................................. G01N 1/22
[52] U.S. Cl. .................,............ 73/863.03; 73/863.61
[58] Field of Search ........... 73/863.01, 863.02, 863.03, 73/863.51, 863.61, 861.52, 861.58, 861.61, 861.62, 864

[56] References Cited

U.S. PATENT DOCUMENTS

| | | | |
|---|---|---|---|
| 2,309,625 | 2/1943 | Cantrell, Jr. ..................... | 73/863.02 |
| 3,377,867 | 4/1968 | Nitesen ............................ | 73/863.03 |
| 3,930,414 | 1/1976 | Russel ............................. | 73/863.03 |
| 4,246,788 | 1/1981 | Olin et al. ........................ | 73/863.03 |

FOREIGN PATENT DOCUMENTS

| | | | |
|---|---|---|---|
| 668227 | 8/1963 | Canada ............................. | 73/863.03 |
| 40-25399 | 11/1965 | Japan ................................ | 73/863.02 |

Primary Examiner—S. Clement Swisher
Assistant Examiner—Tom Noland
Attorney, Agent, or Firm—Joseph H. Schley; Thomas L. Cantrell; Stanley R. Moore

[57] ABSTRACT

Disclosed is an improved proportional gas flow sampler having a combined arrangement of baffles with orifice plates for obtaining proportional flow sampling. Orifice plates may be used alone for this purpose and baffles also may be used alone, but by combining the two, the disadvantages of each are overcome. A spool piece is inserted in the main gas line. In this spool piece a baffle arrangement extracts a fixed fraction of the flow into a bypass line. Downstream of the baffles there are orifice plates in both the main line and the by-pass line. Just upstream of one orifice plate or the other, depending on the gas flow rate, the sample flow is extracted. The sample flow rate typically is a very small percentage of the flow in the main line. The sample flow line also contains an orifice plate. Just upstream of it is a fan and downstream is a control valve. An electronic controller adjusts this valve and fan so that the upstream and downstream pressures at this orifice plate match the corresponding orifice plate pressures in either the main line or by-pass line. When the pressure match is obtained, the sample line flow rate is a reproducible selected fraction of the flow rate in the main line.

3 Claims, 2 Drawing Figures

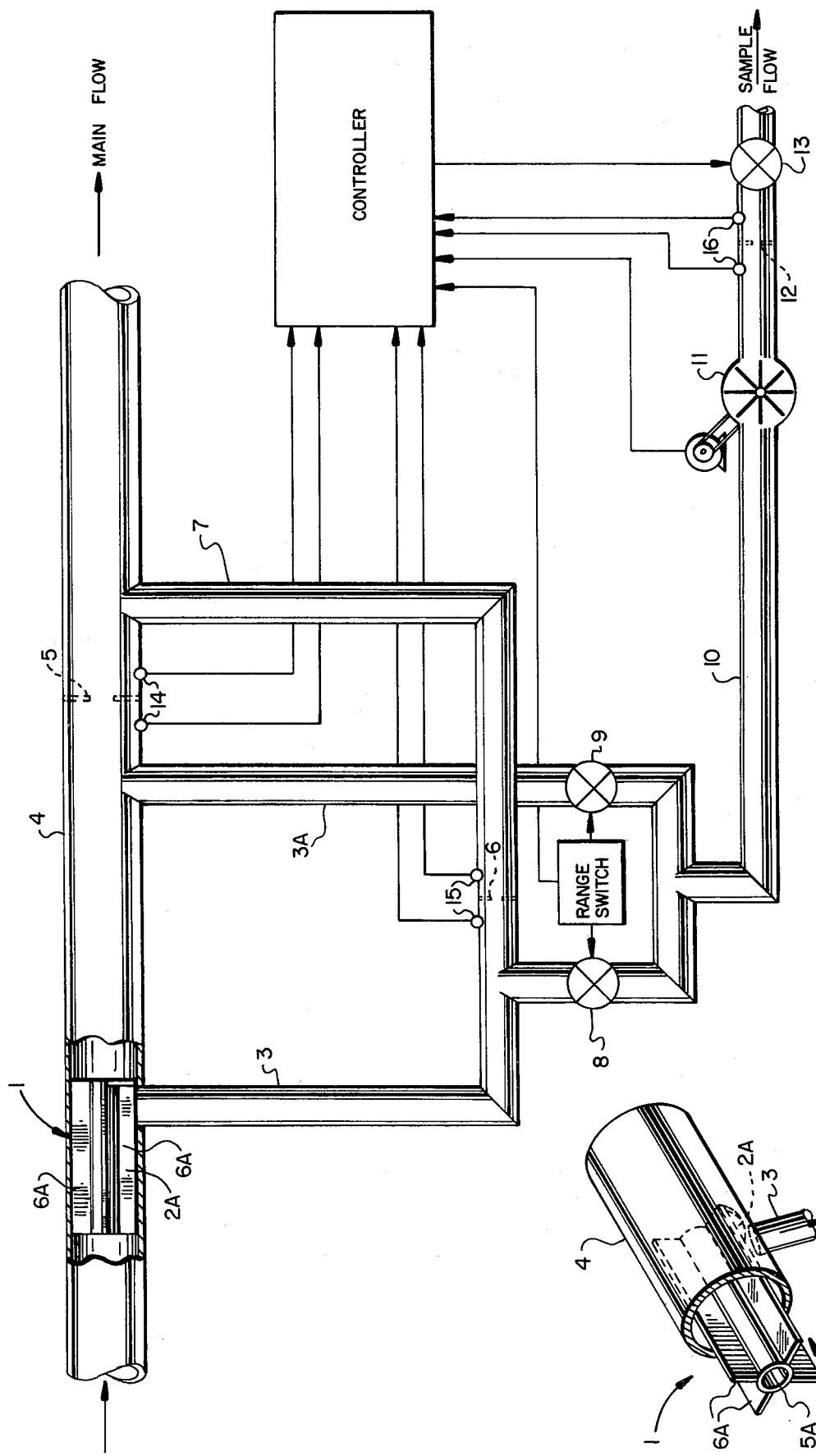

PROPORTIONAL FLOW SAMPLER

BACKGROUND OF THE INVENTION

This invention relates to proportional gas flow sampling equipment, and involves equipment which is particularly adapted for use with or in the equipment disclosed and claimed in copending U.S. patent application Ser. No. 06/272,204 filed June 10, 1981, in the names of William H. Clingman, Jr. and Lyn R. Kennedy, now U.S. Pat. No. 4,396,299, assigned to the same assignee as this application and entitled Method and Apparatus For Determining Total Energy Flow In A Gas Line. While the present invention is useful in other applications as well, the equipment disclosed in said patent application forms a good illustration of a situation in which it is desired to take a proportionally constant flowing sample from a flowing gas stream in a gas line for purposes of making additional measurements of various sorts on it. Proportionality of the sample is important in order to avoid variable calibration factors, and the challenge is to provide equipment which takes a proportionally constant sample over an appreciable range of flow rates in the main gas line.

A baffle arrangement may be provided in a main gas flow line such that a constant proportion of the total flow enters a bypass line upon diversion by the baffle. It is possible to use just baffles for proportional flow sampling, at least over a narrow range of flow rates, and a sampler relying solely on baffles has a very simple piping arrangement. An advantage of the baffle system is that little pressure drop is introduced into the main line. Thus the baffles can be used with "6 ounce" gas in a distribution line. A disadvantage of the baffles is that the proportional cut should not be less than 10–20% of the total flow. If one tries to extract too small a fraction, then changes in the flow profile as a function of Reynolds number will have a significant effect and reduce accuracy.

It is also possible to construct and use a sampler relying solely upon an orifice arrangement without baffles. Such an arrangement is disclosed in the above mentioned patent application. An advantage of the orifice sampling system is that a very small cut can be taken from the main line, such as one part in one thousand.

A disadvantage of either a baffle system or an orifice plate system by themselves is that the dynamic range is limited in an energy flowmeter application. In the latter instrument a proportional flow sampler is combined with a modified titrator-type apparatus for determining energy content or calorific value of the kind generally disclosed in Clingman U.S. Pat. Nos. 3,777,562 issued Dec. 11, 1973; 4,062,236 issued Dec. 13, 1977; 4,125,018 issued Nov. 14, 1978; and, 4,125,123 also issued Nov. 14, 1978. In the energy meter section of the equipment the sample flow is mixed with air and burned. There will only be about a five to one range of flows that can be accomodated with a single burner design. Also, the greater the flow range at the burner the less the inherent accuracy will be.

By combining the baffles with the orifice plates system a two-stage proportional flow sampler is obtained that has both good dynamic range as well as good accuracy.

SUMMARY OF THE INVENTION

In accordance with the invention, an improved apparatus for taking a proportionally constant flowing sample from a gas stream flowing through a main gas flow line at rates subject to variation is provided. It includes a bypass line which extends out of the main gas line and which re-enters the main line downstream from the point of extending out. A orifice plate is mounted in the bypass line. A main sample line is provided which extends out of the bypass line and which extends toward a point of sample processing, for example, a titration-type energy meter. A second orifice plate is mounted in the sample line. Means are provided for detecting the magnitudes of the pressure drops across said orifice plates; such means may be pairs of pressure transducers. Means are also provided for altering the pressure and flow conditions obtained adjacent the second orifice plate to match those obtained at the first orifice plates, to thereby establish flow through the main sample line at a constant proportion of the flow through the main gas flow line.

Preferably, the apparatus also includes a third orifice plate mounted in the main gas line, and an alternate sample line extending out of the main gas flow line at a point upstream of the third orifice plate and extending to the main sample line at a point upstream from the second orifice plate, to provide for sampling at low flow rates in the main gas flow line. Valve means are provided for alternately connecting the bypass line or the alternate sample line to the main sample line.

Preferably baffle means are mounted in the main gas flow line for directing gas flowing therein into the bypass line. The baffle means divide the flow area in the main gas flow line into a plurality of areas, and direct the gas flowing through one or more of the areas into the bypass line.

Preferably the means for altering pressure and flow conditions adjacent the third orifice plate include a variable speed fan in the sample line upstream of said third orifice plate, and a variable throat valve in the sample line downstream of the third orifice plate.

Stated more broadly, the invention involves, in a sampling system of the kind just outlined, the provisions of means for establishing and maintaining a substantially uniform flow rate profile at a selected point in said main gas flow line; and means for mechanically dividing out of said main gas flow line at said point a flowing sample by dividing the area of said line into a plurality of areas and directing the gas flowing through at least one of said areas out of said line.

DESCRIPTION OF THE DRAWINGS

FIG. 1 is somewhat diagrammatic side elevational view, with parts partly broken away, of a preferred embodiment of a flow sampler constructed in accordance with the invention; and FIG. 2 is a fragmentary perspective view of a baffle assembly constructed in accordance with the invention shown installed in a main gas flow line.

DESCRIPTION OF THE PREFERRED EMBODIMENTS

Referring to FIG. 1, there is a baffle system 1 in the main line 4. The baffle includes an open-ended cylinder 5A which is mounted concentric with the main pipeline. This cylinder is two to three pipe diameters in length and is supported in the pipe by radially oriented baffles 6A. These baffles and the concentric cylinder divide the flow into five compartments; one of these, 2A, is closed on the downstream side of the baffles and cylinders.

The flow in this compartment is directed through the by-pass line 3. At Reynolds numbers above 5000 the arrangement of baffles just described extracts a substantially constant proportion of flow from the main line. The magnitude of the proportion depends on the cross-sectional area of compartment 2A in comparison with the total cross-sectional area of the pipe. Preferably it should be about 20% of the total flow. There is a minimum Reynolds number required in order to have a reasonably uniform flow profile, and this minimum is about 5000.

Downstream from the baffles in both the main line and the by-pass line are orifice plates 5 and 6. These are sized and arranged so that the downstream pressure at main line orifice 5 is always a little less than at by-pass orifice 6. As a result, most of the by-pass flow will be returned to the main line through conduit 7.

There are sample line ports just upstream of the orifice plates 5 and 6. Valves 8 and 9 in these sample ports are either open or closed. One valve is always open and the other is always closed. These valves are controlled by the range switch. Downstream of valves 8 and 9 the proportional flow sample is led through conduit 10 to fan 11, orifice 12, and control valve 13. Both the fan and control valve are operated by the controller as described below. The controller uses signals from three pairs of pressure transducers, 14, 15 and 16 in conduit lines 4, 3 and 10.

The controller increases or decreases the speed of fan 11 to thereby match the upstream pressure at orifice 12 with that at either 5 or 6. The controller also operates valve 13 to open or close it to a greater or lesser extent so that the corresponding downstream pressures also match. Then, with the appropriate orifice design, the flow through orifice 12 will always be in the same proportion to that through orifices 5 or 6.

In operation, the range switch is used to change the proportion of the main gas flow which is being sampled. This is done to hold the sample flow within boundaries that can be accomodated by the combustion apparatus to which the sample is delivered in a total energy measuring apparatus. For example, assume that during the day the main gas flow is 2000 to 10,000 SCFH (Standard Cubic Feet per Hour) and that at night it is 400 to 2000 SCFH. This would be typical for the flow of gas entering a commercial establishment. During the day valve 8 is open and valve 9 is closed. Assume that the orifices are designed to take a one part in two hundred cut and the baffles 6 a one part in five cut. Then the sample line flow would then vary between 2 SCFH and 10 SCFH. At night valve 8 is closed and valve 9 is open. The sample line flow first passing through line 3A would still vary from 2 SCFH to 10 SCFH.

This flow rate is within an optimum range for the burner design in the combustion apparatus that is downstream of the sample taking equipment. Without the range switch, a 2–10 SCFH flow during the day would fall to 0.4–2 SCFH at night. The burner flames would likely become extinguished because of insufficient fuel flow. Limiting the gas flow range in the combustion apparatus to a relatively narrow range also increases the overall accuracy of the instrument.

The fan 11 overcomes the pressure drops in the plumbing between it and the main line. The design can also be used in a system in which there is a very low pressure in the main gas line. In this case the three orifice plates 5, 6 and 12 would have larger openings and the fan would furnish the driving energy in the sample line plumbing.

From the foregoing it can be seen that there is provided, in accordance with the present invention, a very simple sampling method and apparatus for producing a proportionally constant flowing sample from a flowing stream of gas moving through a main gas flow line.

We claim:

1. Apparatus for taking a proportionally constant flowing sample from a gas stream flowing through a main gas flow line at rates subject to variation comprising:
 a bypass line extending out of said main gas line and reentering said main line downstream from the point of said extending out;
 a first orifice plate mounted in said bypass line;
 a main sample line extending out of said bypass line and extending toward a point of sample processing;
 a second orifice plate mounted in said sample line;
 a third orifice plate mounted in said main gas line;
 an alternate sample line extending out of said main gas flow line at a point upstream of said third orifice plate and extending to said main sample line at a point upstream from said second orifice plate.
 means for detecting the magnitudes of the pressure drops across said orifice plates;
 means for altering the pressure and flow conditions obtained adjacent said second orifice plate to match those obtained at said first orifice plate, to thereby establish flow through said main sample line at a constant proportion of the flow through said main gas flow line.

2. Apparatus in accordance with claim 1 in which said means for altering the pressure and flow conditions obtained at said second orifice plate is adapted to also selectively match said pressure and flow conditions to those obtained at said third orifice plate.

3. Apparatus in accordance with claim 1 and further comprising valve means for alternately connecting said bypass line or said alternate sample line to said main sample line.